United States Patent
Wogoman

(10) Patent No.: US 7,122,102 B2
(45) Date of Patent: *Oct. 17, 2006

(54) ELECTROCHEMICAL SENSOR

(75) Inventor: Frank W. Wogoman, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 142 days.

This patent is subject to a terminal disclaimer.

(21) Appl. No.: 10/156,572

(22) Filed: May 29, 2002

(65) Prior Publication Data

US 2002/0185375 A1    Dec. 12, 2002

Related U.S. Application Data

(60) Provisional application No. 60/297,023, filed on Jun. 11, 2001.

(51) Int. Cl.
*G01N 27/403* (2006.01)
*G01N 27/333* (2006.01)
*G01N 27/327* (2006.01)

(52) U.S. Cl. .................. 204/400; 204/403.01; 204/416

(58) Field of Classification Search .............. 204/400, 204/403, 416, 418, 429, 403.01, 403.15
See application file for complete search history.

(56) References Cited

U.S. PATENT DOCUMENTS

| 4,534,825 A | * | 8/1985 | Koning et al. ................. 438/49 |
| 4,816,123 A | | 3/1989 | Ogan et al. ............. 264/272.13 |
| 5,798,031 A | | 8/1998 | Charlton et al. |
| 5,958,199 A | | 9/1999 | Miyamoto et al. |
| 6,299,757 B1 | * | 10/2001 | Feldman et al. ............ 205/775 |

FOREIGN PATENT DOCUMENTS

| EP | 121579 A2 | 8/2003 |
| EP | 121579 A3 | 8/2003 |
| WO | WO 95/33504 | 12/1995 |

OTHER PUBLICATIONS

U.S. Appl. No. 60/254,626.*
Dharmatilleke, D. et al., Three-Dimensional Silicone Device Fabrication and Inter-Connection Scheme for Microfluidic Application Using Sacrificial Wax Layers MEMS-vol. 2, 2000 pp. 413-418.

* cited by examiner

*Primary Examiner*—Alex Noguerola

(57) ABSTRACT

An electrochemical sensor with a capillary channel is formed by placing a sacrificial insert on a sensor base and applying casting material. After the casting material is cured, the sacrificial is removed leaving a capillary channel in the sensor. The insert may be removed by a tool including a clamp for clamping and holding the insert stationary and a sliding block to which the sensor is secured.

4 Claims, 1 Drawing Sheet

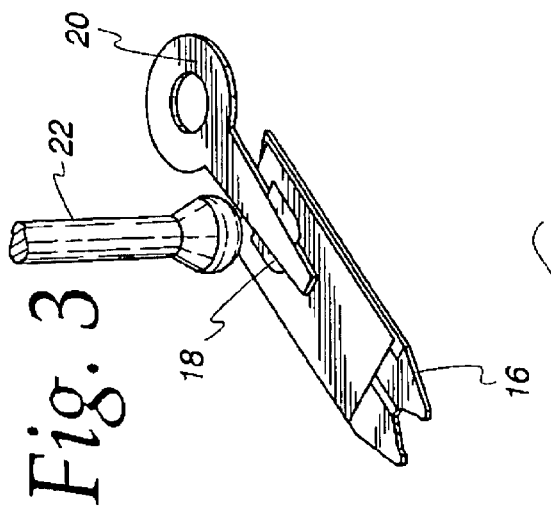
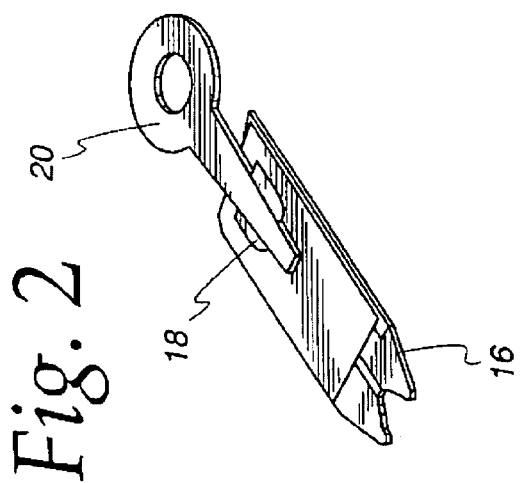
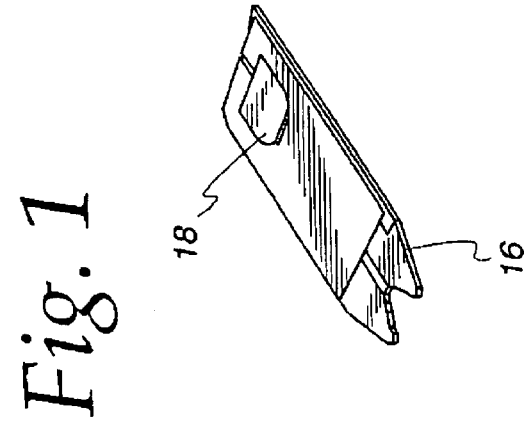
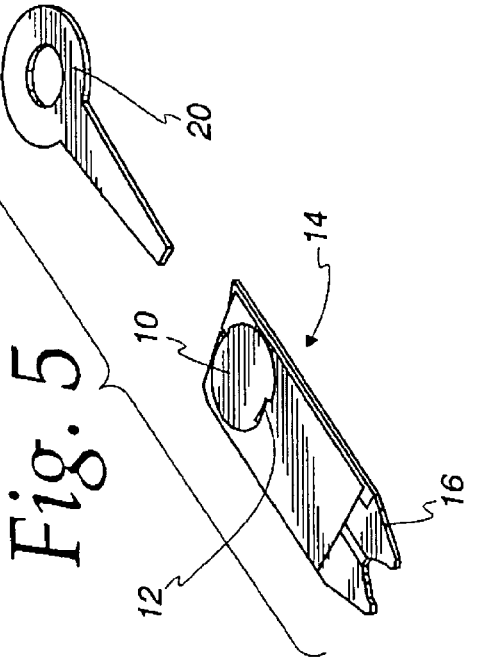
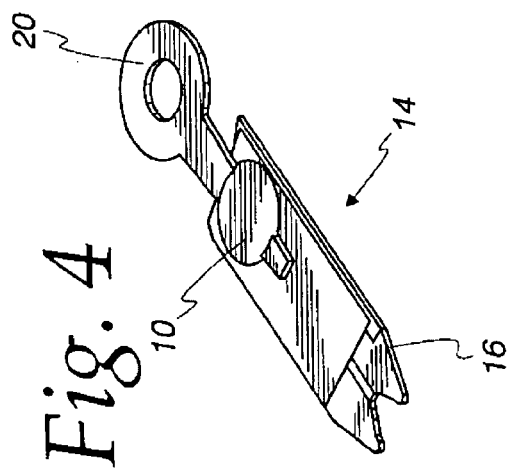

ELECTROCHEMICAL SENSOR

RELATED APPLICATION

This application claims the benefit of the U.S. Provisional Application 60/297,023, filed on Jun. 11, 2001, which is hereby incorporated by reference in its entirety.

FIELD OF THE INVENTION

The present invention relates generally to electrochemical sensors, and more, particularly, to electrochemical sensors with capillary channels formed by sacrificial inserts, and a method of making these sensors.

BACKGROUND OF THE INVENTION

Electrochemical sensors are used for the quantification of components or analytes in a sample of liquid such as blood or urine. Sensors of this type are disclosed in U.S. Pat. Nos. 5,958,199 and 5,798,031. These sensors include an insulating base with carbon electrodes printed on the base. The electrodes are covered with a reagent and are located in a capillary channel. The capillary channel is defined by a spacer positioned between the base and a cover piece.

Other electrochemical sensors have two parts, a base and a lid. The lid forms three sides of a capillary space and the base forms the fourth. The base and lid are laminated together to form the sensor.

Sensors of this type are used by dipping an open end of the capillary channel into test liquid. The liquid is drawn by capillary action into the capillary channel to cover a reagent and/or enzyme in the capillary channel near one or more electrodes. A measurement of an analyte in the test liquid can then be made. The usual way to fabricate sensors of this type is to precision screen print active areas within a capillary area formed by a shaped top lid. It is desirable to reduce the cost and assembly required by this construction. Moreover, it is difficult to provide electrodes in a small molded capillary channel of less than 0.005 inches in height and it is desirable to provide a sensor of this size with molded electrodes so that such a sensor could be used for electrochemical analysis.

SUMMARY OF THE INVENTION

The present invention is directed to an electrochemical sensor and to the method for making the sensor. The sensor of the present invention includes a capillary channel of approximately 0.005 inch in height that is formed by a sacrificial insert in a casting process. Electrodes may be printed and reagent applied on a sensor base and a sacrificial or protective insert is placed over the printed electrodes and reagent. Casting material is then applied over the insert. Once the casting material is cured, the insert is removed leaving a capillary channel and lid.

BRIEF DESCRIPTION OF THE DRAWINGS

Other objects and advantages of the invention will become apparent upon reading the following detailed description and upon reference to the drawings in which:

FIG. 1 is a perspective view of a base sheet or base of an electrochemical biosensor;

FIG. 2 is a view similar to FIG. 1 with a sacrificial protective insert in position over printed circuits on the base sheet;

FIG. 3 is a view similar to FIG. 2 with a casting material dispenser in position to dispense casting material;

FIG. 4 is a perspective view of the biosensor with the casting material on the biosensor; and FIG. 5 illustrates the insert removed from the casting material;

While the invention is susceptible to various modifications and alternative forms, specific embodiments thereof have been shown by way of examples in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE PREFERRED EMBODIMENTS

Referring to FIGS. 1–5, there is illustrated the formation of a lid 10 and capillary channel for an electrochemical biosensor 14. Existing biosensor construction requires that a spacer and a lid or a formed lid be bonded to produce a capillary channel necessary for sensor operation. The method of the present invention utilizes a casting process whereby the capillary channel 12 and the lid 10 are produced in one operation.

The formation of the biosensor 14 starts with a standard base sheet 16 having a precision screen printed active area 18 that is standard in current biosensors (FIG. 1). A protective or sacrificial insert 20 is placed over the active area 18 where the capillary channel 12 is required (FIG. 2). A dispenser 22 for dispensing casting material is positioned over the insert 20 above the printed active area 18 (FIG. 3), and casting material is dispensed over the insert 20 and the printed active area 18 (FIG. 4). After the casting material has cured, it has formed the lid 10. At this time the insert 20 may be removed from the casting material or lid 10 and the base sheet 16 leaving the very small capillary channel 12. This process produces very small, precise and reproducable capillary channels at low cost.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. An electrochemical sensor, comprising:
   a sensor base including a screen-printed active area with at least one electrode;
   a sacrificial insert on said sensor base; and
   casting material on said sensor base and over said sacrificial insert, said casting material of a formulation which allows for mechanical removal of said sacrificial insert from said casting material and said sensor base leaving a capillary channel in said casting material, wherein said sacrificial insert is adapted to he mechanically removed to form the capillary channel.

2. The electrochemical sensor of claim 1 wherein the at least one electrode is a plurality of electrodes and wherein the plurality of electrodes is in said capilary channel.

3. The electrochemical sensor of claim 1 further comprising a reagent in said capillary channel.

4. The electrochemical sensor of claim 1 wherein said capillary channel has a height of about 0.005 inch.

* * * * *